United States Patent [19]

Sakai et al.

[11] Patent Number: 4,686,187

[45] Date of Patent: Aug. 11, 1987

[54] PROCESS FOR PREPARING PECTIN FROM PLANT TISSUES

[76] Inventors: Takuo Sakai, 13-6, Harayamadai, 4-Cho 590-01; Tohoru Katsuragi, 2-52, Ohnoshibatakusha, 23, Ohnoshiba-Cho 593, both of Sakai-shi, Osaka, Japan

[21] Appl. No.: 253,929

[22] PCT Filed: Aug. 8, 1980

[86] PCT No.: PCT/JP80/00179
§ 371 Date: Apr. 3, 1981
§ 102(e) Date: Apr. 3, 1981

[87] PCT Pub. No.: WO81/00417
PCT Pub. Date: Feb. 19, 1981

[30] Foreign Application Priority Data

Aug. 10, 1979 [JP] Japan .................. 54-102389

[51] Int. Cl.⁴ ............................................ G08B 30/04
[52] U.S. Cl. ..................... 435/275; 435/911; 426/49; 426/50; 426/52
[58] Field of Search ............ 435/267, 940, 938, 930, 435/944, 921, 275, 911; 426/49, 50, 42

[56] References Cited

U.S. PATENT DOCUMENTS 2,387,635 10/1945 Bailey .................. 435/275
3,063,911 11/1962 Tanaka et al. ............ 435/225

FOREIGN PATENT DOCUMENTS 4070495 6/1979 Japan .................. 435/275

OTHER PUBLICATIONS

Eddy, from Biochemistry of Industrial Microorganisms, Rainbow et al, eds., Academic Press, London, 1963, pp. 494-495.

Laskin et al, Handbook of Microbiology, condensed edition, CRC Press, Cleveland, 1974, p. 413.

*Primary Examiner*—Christine M. Nucker
*Attorney, Agent, or Firm*—Stiefel, Gross, Kurland & Pavane

[57] ABSTRACT

A process for preparing pectin, which is useful for foods and medicines or the like, by subjecting a plant tissue containing pectic substances to the action of a microorganism which belongs to the genus Endomyces, Endomycopsis, Saccharomyces, Shizosaccharomyces, Pichia, Hansenula, Debaryomyces, Hanseniaspora, Torulopsis, Candida or Kluyveromyces and possesses an activity liberating pectin from a plant tissue; or of a culture broth or processed material thereof to liberate pectin from said plant tissue; and recovering pectin.

3 Claims, No Drawings

PROCESS FOR PREPARING PECTIN FROM PLANT TISSUES

The present invention relates to a useful method for the isolation of pectin from plant tissues with the use of particular yeasts.

Pectin is a useful polysaccharide utilized as a raw material for foods, medicines or cosmetics, which is contained in higher plants in large amounts. Hitherto, the production of pectin has been carried out by heat-extracting a plant tissue containing pectic substances in the presence of a chelating agent, an acid or the like. However, such methods cause difficulty in the isolation of pectin and problems in the treatment of residues.

The present inventors have repeatedly studied methods for producing pectin under mild conditions, instead of the known chemical methods mentioned above, and have previously found that *Trichosporon penicillatum* SNO-3, belonging to the genus Trichosporon, produces an enzyme which is able to liberate pectin from various plant tissues, without rupturing the tissues (Japanese Unexamined Patent Publication No. 70495/1979). In that application, a process for preparing pectin by subjecting a plant tissue containing pectin as a component to the actions of a microorganism which belongs to the genus of Trichosporon and possesses an activity of liberating pectin from a plant tissue, a culture broth of said microorganism and its extract is claimed. As the result of a further development for the above studies, it was found that various yeasts possess an activity of liberating pectin from plant tissues containing pectic substances, which is the basis of the present invention.

Thus, according to the present invention, there is provided a process for preparing pectin, which is characterized by subjecting a plant tissue containing pectic substances to the action of a microorganism which belongs to the genus Endomyces, Endomycopsis, Saccharomyces, Schizosaccharomyces, Pichia, Hansenula, Debaryomyces, Hanseniaspora, Torulopsis, Candida or Kluyveromyces and possesses an activity liberating pectin from a plant tissue; or of a culture broth or processed material thereof to liberate pectin from said plant tissue; and recovering the pectin.

The microorganisms used in the invention are sporogeneous or sporogenous yeasts. Examples thereof are as follows.

The microorganisms belonging to Endomyces are *Endomyces geotrichum* and *Endomyces lindneri;* those belonging to Endomycopsis are *Endomycopsis capsularis* and *Endomycopsis vernalis;* those belonging to Saccharomyces are *Saccharomyces uvarum, Saccharomyces bailii, Saccharomyces delbrueckii* and *Saccharomyces fermentati;* those belonging to Schizosaccharomyces is *Schizosaccharomyces octosporus;* those belonging to Pichia are *Pichia orientalis, Pichia polymorpha* and *Pichia farinosa;* those belonging to Hansenula are *Hansenula saturnus* and *Hansenula minuta;* those belonging to Debaryomyces are *Debaryomyces hansenii* and *Debaryomyces castellii;* those belonging to Hanseniaspora are *Hanseniaspora valbyensis* and *Hanseniaspora uvarum;* those belonging to Torulopsis are *Torulopsis sphaerica* and *Torulopsis pinus;* those belonging to Candida are *Candida krusei, Candida glaebosa* and *Candida macedoniensis;* those belonging to Kluyveromyces are *Kluyveromyces fragilis, Kluyveromyces lactis, Kluyveromyces marxianus* and *Kluyveromyces drosophilarum;* and strains similar to these strains and mutants thereof. The term "strains similar to these strains" mentioned above means those which possess a pectin-liberating activity and have mycological properties similar to those of these strains. The term "mutants thereof" also includes any of the mutants of the specifically exemplified strains and strains similar thereto which are artifically induced by chemical or physical means or are spontaneously induced. Artificial means which may be used for the mutation are those known in the art.

The present invention also depends upon the discovery that yeast microorganisms contain an enzyme which is capable of liberating pectin.

Any strains to be included in the above-mentioned genera, insofar as they contain such an enzyme, are within the scope of the present invention.

For the isolation of pectin from a plant tissue according to the method of the present invention, the above microorganisms may be directly inoculated into a plant tissue to be treated and cultured under static, agitating or shaking conditions in accordance with conventional methods; or a culture broth which is obtained by cultivating the above microorganism or processed material thereof may be contacted with a plant tissue. Media to be used for the cultivation of the microorganism, i.e., the seed cultivation is not particularly limited and may be any one which contains the various nutrients normally used in the conventional cultivation of yeasts. The usual media may suitably contain peptone, casein hydrolysate, yeast extract and glucose and, if circumstances require, inorganic salts, such as phosphates, magnesium salts or potassium salts. Certain kinds of plant tissues may also be used as the seed cultivation medium, without the addition of any nutrients but after heat sterilization.

The peel or segment cover of citrus fruits is an especially advantageous medium for this purpose.

The cultivation conditions for the microorganism in the above-mentioned medium, are properly determined to maximize the quantity of production of the intended enzyme, usual conditions being 20°–37° C. for 10–50 hours. The cultivation may be with shaking, static or aeration-stirring or in a solid state. Under such cultivation conditions, mycelium is grown and an enzyme is liberated from the mycelium. The cultivation broth may be utilized as such or as processed material, as a concentrate or as a solution of purified enzyme. The concentrate may be obtained by subjecting the cultivation broth, which is, if necessary, filtered, to a treatment under mild conditions, e.g., evaporating the broth at a low temperature and low pressure or concentrating the broth by the use of an ultra-filtration membrane. The solution of purified enzyme may also be obtained from the broth, e.g., which is filtrated, concentrated and then subjected to repeated fractional precipitation by the addition of ammonium sulphate; alternatively, it may be filtered and subjected to CM."Sephadex" column chromatography and then to "Sephadex" G-75 gel filtration.

The mechanism involved in the method of the present invention is considered to be one in which an enzyme produced from the yeast penetrates into a plant tissue, acts on pectic substances, especially water-insoluble protopectin, and produces water-soluble pectin, pectin thereby being liberated from the plant tissue.

Pectin liberated from plant tissue by the method of the present invention may be isolated in accordance with conventional methods. For example, the solution, treated as mentioned above, is filtered and the filtrate is mixed with three times its volume of a water-miscible organic solvent, e.g., ethanol, to precipitate out pectin. The collected pectin is washed with a solvent similar to the above organic solvent, e.g., ethanol, and dried to give pectin of high purity.

Pectin thus obtained has a molecular weight of more then 100,000, irrespective of the kind of yeast used. The pectins are different from those obtained by the known chemical methods. They possess a narrow molecular weight distribution and are similar to natural pectin. Furthermore, the pectin is suitable for use as a food or medicine, since it does not contain chemical substances. In addition, the properties of pectins obtained by the invention vary more or less, according to the nature of the raw materials.

The present invention relates to the method of obtaining a high purity of pectin in a simple way and in a high yield from plant tissues, by the utilization of yeast microorganisms, as described above, and also to a method which can be utilized for the removal of pectin from plant tissues or for the production of an extract of plant containing pectin.

Furthermore, the plant tissues used in the treatment of the present invention are preferably those available at a low price and with as high a pectin content as possible, although they are not particularly limited thereto. Examples are citrus fruits, such as *Citrus unshiu, Citrus natsu-daidai*, lemon, grapefruit, navel orange or the like. Any of the peels and the segment covers of these citrus fruits may be used as the raw material. It is also possible to use the residue which is obtained by pressing citrus fruits to obtain fruit juice, and which is, therefore, cheap and serves as a utilization of waste material.

The invention is illustrated by the following examples:

EXAMPLE 1

500 g of finely cut fresh peel of *Citrus unshiu* were suspended in 1 l of sterilized water in a sterilized flask, and 50 ml of each of the cultivation broths of the various strains of Table 1 were added to the suspension. The resultant was incubated at 30° C. for 24 hours with occasional stirring, and filtered through a gauze. To the supernatant was added three times its volume of ethanol to precipitate pectin, followed by drying it in vacuo. The results obtained are shown in Table 1.

Each of the seed cultivations was conducted with the use of a medium (pH 5.0) containing 0.5% of peptone, 3% of glucose, 0.2% of $CaCl_2$, 0.1% of $KH_2PO_4$, 0.05% of $MgSO_4.7H_2O$ at 30° C. for 24 hours, with shaking.

EXAMPLE 2

Each of various strains used in Example 1 was cultivated under the same condition as in Example 1, except for prolonging it to 36 hours. 300 g of segment cover of *Citrus natsudaidai* were added to 300 ml of each of the cultivation filtrates and incubated, with shaking, at 30° C. for 6 hours. The reaction solution was filtered and three times its volume of ethanol were added to the filtrate to precipitate the pectin obtained. It was collected and dried in vacuo. The yields are shown in Table 2.

EXAMPLE 3

*Kluyveromyces marxianus* (IFO 0277) was cultivated under the same conditions as in Example 1. 100 g of each of various plant tissues were added to 100 ml of the cultivation filtrate broth and incubated for 3 hours, followed by the same treatments as in Example 1, to give pectin. The yields are as shown in Table 3.

EXAMPLE 4

In accordance with the method of Example 1, *Endomycopsis capsularis* (IFO 0672) was allowed to act on the peel of *Citrus unshiu*. The treated solution was filtered and to the filtrate was added three times its volume of ethanol, to precipitate pectin. It was collected, washed well with ethanol and dried to give pectin having the properties shown in Table 4.

TABLE 1

| Yields of pectin obtained from the peel of *Citrus unshiu* | |
|---|---|
| Strain | Yield of pectin |
| Candida krusei IFO 0013 | 4.0 (g) |
| Candida glaebosa IFO 1353 | 0.7 |
| Candida macedoniensis AKU 4587 | 0.7 |
| Debaryomyces hansenii IFO 0794 | 4.2 |
| Debaryomyces castellii IFO 1359 | 0.5 |
| Endomyces geotrichum IFO 9541 | 6.8 |
| Endomyces lindneri AKU 4206 | 0.8 |
| Hanseniaspora valbyensis IFO 0115 | 3.0 |
| Hanseniaspora uvarum IFO 1413 | 0.5 |
| Hansenula saturnus IFO 0117 | 4.5 |
| Hansenula minuta IFO 0975 | 4.0 |
| Kluyveromyces fragilis IFO 0288 | 6.3 |
| Kluyveromyces lactis IFO 1090 | 4.0 |
| Kluyveromyces marxianus IFO 0277 | 9.0 |
| Kluyveromyces drosophilarum IFO 1012 | 4.0 |
| Pichia orientalis IFO 1279 | 3.2 |
| Pichia polymorpha AKU 4250 | 0.6 |
| Pichia farinosa AKU 4251 | 0.6 |
| Saccharomyces uvarum IFO 0565 | 3.0 |
| Saccharomyces bailii IFO 1047 | 3.0 |
| Saccharomyces delbrueckii IFO 0285 | 4.2 |
| Saccharomyces fermentati IFO 0422 | 4.8 |
| Schizosaccharomyces octosporus IFO 0353 | 4.1 |
| Torulopsis sphaerica IFO 0648 | 5.3 |
| Torulopsis pinus IFO 0741 | 0.8 (g) |
| Enxomycopsis capsularis IFO 0672 | 7.5 |
| Endomycopsis vernalis AKU 4210 | 0.5 |

TABLE 2

| Yields of pectin obtained from the segment cover of *citrus natsudaidai* | |
|---|---|
| Strain | Yield of pectin |
| Candida krusei IFO 0013 | 2.5 (g) |
| Debaryomyces hansenii IFO 0794 | 2.3 |
| Endomyces geotrichum IFO 9541 | 3.7 |
| Hanseniaspora valbyensis IFO 0115 | 1.6 |
| Hansenula saturnus IFO 0117 | 2.2 |
| Hansenula minuta IFO 0975 | 1.9 |
| Kluyveromyces fragilis IFO 0288 | 3.5 |
| Kluyveromyces lactis IFO 1090 | 2.8 |
| Kluyveromyces marxianus IFO 0277 | 5.0 |
| Kluyveromyces drosophilarum IFO 1012 | 2.4 |
| Pichia orientalis IFO 1279 | 1.5 |
| Saccharomyces uvarum IFO 0565 | 1.3 |
| Saccharomyces bailii IFO 1047 | 1.5 |
| Saccharomyces delbrueckii IFO 0285 | 2.9 |
| Saccharomyces fermentati IFO 0422 | 3.0 |
| Schizosaccharomyces octosporus IFO 0353 | 2.2 |
| Torulopsis sphaerica IFO 0648 | 2.3 |
| Endomycopsis capsularis IFO 0672 | 4.0 |

TABLE 3

Yields of pectin obtained from the peel or segment cover of citrus fruits by the use of *Kluyveromyces marxianus* IFO 0277

| Fruit | Yield of pectin |
| --- | --- |
| Navel orange | |
| Peel | 1.9 (g) |
| Segment cover | 1.6 |
| Grapefruit | |
| Peel | 1.9 |
| Segment cover | 1.3 |
| *Citrus unshiu* | |
| Peel | 1.8 |
| Segment cover | 1.2 |
| *Citrus natsudaidai* | |
| Peel | 1.9 |
| Segment cover | 1.7 |
| Lemon | |
| Peel | 1.0 |
| Segment cover | 1.1 |

TABLE 4

Properties of pectin obtained from the peel of *Citrus unshiu* by the use of *Endomycopsis capsularis* IFO 0672

| | |
| --- | --- |
| Moisture | 8.6% |
| Ash* | ≦0.01% |
| Methoxylated carboxyl group | 85.4% |
| Galacturonic acid | 75.0% |
| Neutral sugar | 25.0% |
| Relative viscosity (0.1% solution) | 1.52 |
| pH (0.5% solution) | 3.3 |
| Molecular weight** | 105,000 |
| Found values by elementary analysis | C: 40.25, H: 5.78 and N: 0.60% |

*Measured on a sample without ion exchange treatment.
**Determined by the method of Smit and Bryant [J. Food Science, 32, 197, (1967)].

We claim:

1. A process for preparing pectin comprising subjecting a plant tissue containing pectin substances to the action of a microorganism selected from *Kluyveromyces fragilis* IFO 0288 or *Kluyveromyces marxianus* IFO 0277 which possesses an activity of liberating pectin from a plant tissue or to the action of a culture broth or processed material of said microorganism which possesses an activity of liberating pectin from plant tissue to liberate pectin from said plant tissues, and recovering the pectin.

2. A process as described in claim 1, wherein the peel or segment cover of citrus fruits is used as the plant tissue containing pectic substances.

3. A process as described in claim 2, wherein the citrus fruit is *Citrus unshiu, Citrus natsudaidai*, grapefruit, orange or lemon.

* * * * *